United States Patent
Carr, Jr.

(10) Patent No.: US 8,437,834 B2
(45) Date of Patent: May 7, 2013

(54) BREAST MARKER

(75) Inventor: Robert M. Carr, Jr., Paradise Valley, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 13/247,403

(22) Filed: Sep. 28, 2011

(65) Prior Publication Data

US 2012/0078238 A1    Mar. 29, 2012

Related U.S. Application Data

(63) Continuation of application No. 12/446,644, filed as application No. PCT/US2007/081399 on Oct. 15, 2007, now Pat. No. 8,064,987.

(60) Provisional application No. 60/853,633, filed on Oct. 23, 2006.

(51) Int. Cl.
*A61B 6/00* (2006.01)
*A61B 5/05* (2006.01)

(52) U.S. Cl.
USPC .......................................... 600/431; 600/426

(58) Field of Classification Search .......... 600/425–426, 600/431–435; 604/19
See application file for complete search history.

(56) References Cited

U.S. PATENT DOCUMENTS

| | | | |
|---|---|---|---|
| 2,192,270 A | 3/1940 | McGowan | |
| 2,481,408 A | 9/1949 | Fuller et al. | |
| 2,832,888 A | 4/1958 | Houston | |
| 2,899,362 A | 8/1959 | Sieger, Jr. et al. | |
| 2,907,327 A | 10/1959 | White | |
| 3,341,417 A | 9/1967 | Sinaiko | |
| 3,402,712 A | 9/1968 | Eisenhand | |
| 3,516,412 A | 6/1970 | Ackerman | |
| 3,593,343 A | 7/1971 | Viggers | |
| 3,757,781 A | 9/1973 | Smart | |
| 3,818,894 A | 6/1974 | Wichterle et al. | |
| 3,823,212 A | 7/1974 | Chvapil | |
| 3,921,632 A | 11/1975 | Bardani | |
| 4,005,699 A | 2/1977 | Bucalo | |
| 4,007,732 A | 2/1977 | Kvavle et al. | |
| 4,041,931 A | 8/1977 | Elliott et al. | |
| 4,103,690 A | 8/1978 | Harris | |
| 4,105,030 A | 8/1978 | Kercso | |
| 4,172,449 A | 10/1979 | LeRoy et al. | |

(Continued)

FOREIGN PATENT DOCUMENTS

| | | |
|---|---|---|
| DE | 1029528 B | 5/1958 |
| EP | 0146699 A1 | 7/1985 |

(Continued)

OTHER PUBLICATIONS

Armstong, J.S., et al., "Differential marking of Excision Planes in Screened Breast lesions by Organically Coloured Gelatins", Journal of Clinical Pathology, Jul. 1990, No. 43 (7) pp. 604-607, XP000971447 abstract; tables 1,2.

(Continued)

*Primary Examiner* — Victoria P Shumate

(57) ABSTRACT

Tissue markers, systems for marking tissue, and methods of using tissue markers. A tissue marker may have a body with a first surface and a second surface, a plurality of coupling sites, and a plurality of elongate members. The tissue marker may include a remotely visible material. The tissue marker may have a delivery configuration that is different from a deployed configuration.

11 Claims, 4 Drawing Sheets

U.S. PATENT DOCUMENTS

| | | |
|---|---|---|
| 4,197,846 A | 4/1980 | Bucalo |
| 4,217,889 A | 8/1980 | Radovan et al. |
| 4,276,885 A | 7/1981 | Tickner et al. |
| 4,294,241 A | 10/1981 | Miyata |
| 4,298,998 A | 11/1981 | Naficy |
| 4,331,654 A | 5/1982 | Morris |
| 4,390,018 A | 6/1983 | Zukowski |
| 4,400,170 A | 8/1983 | McNaughton et al. |
| 4,401,124 A | 8/1983 | Guess et al. |
| 4,405,314 A | 9/1983 | Cope |
| 4,428,082 A | 1/1984 | Naficy |
| 4,438,253 A | 3/1984 | Casey et al. |
| 4,442,843 A | 4/1984 | Rasor et al. |
| 4,470,160 A | 9/1984 | Cavon |
| 4,487,209 A | 12/1984 | Mehl |
| 4,545,367 A | 10/1985 | Tucci |
| 4,549,560 A | 10/1985 | Andis |
| 4,582,061 A | 4/1986 | Fry |
| 4,582,640 A | 4/1986 | Smestad et al. |
| 4,588,395 A | 5/1986 | Lemelson |
| 4,597,753 A | 7/1986 | Turley |
| 4,647,480 A | 3/1987 | Ahmed |
| 4,655,226 A | 4/1987 | Lee |
| 4,661,103 A | 4/1987 | Harman |
| 4,682,606 A | 7/1987 | DeCaprio |
| 4,693,237 A | 9/1987 | Hoffman et al. |
| 4,740,208 A | 4/1988 | Cavon |
| 4,813,062 A | 3/1989 | Gilpatrick |
| 4,820,267 A | 4/1989 | Harman |
| 4,832,680 A | 5/1989 | Haber et al. |
| 4,832,686 A | 5/1989 | Anderson |
| 4,847,049 A | 7/1989 | Yamamoto |
| 4,863,470 A | 9/1989 | Carter |
| 4,870,966 A | 10/1989 | Dellon et al. |
| 4,874,376 A | 10/1989 | Hawkins, Jr. |
| 4,889,707 A | 12/1989 | Day et al. |
| 4,909,250 A | 3/1990 | Smith |
| 4,938,763 A | 7/1990 | Dunn et al. |
| 4,950,665 A | 8/1990 | Floyd |
| 4,963,150 A | 10/1990 | Brauman |
| 4,970,298 A | 11/1990 | Silver et al. |
| 4,989,608 A | 2/1991 | Ratner |
| 4,994,028 A | 2/1991 | Leonard et al. |
| 5,012,818 A | 5/1991 | Joishy |
| 5,059,197 A | 10/1991 | Urie et al. |
| 5,081,997 A | 1/1992 | Bosley, Jr. et al. |
| 5,120,802 A | 6/1992 | Mares et al. |
| 5,125,413 A | 6/1992 | Baran |
| 5,137,928 A | 8/1992 | Erbel et al. |
| 5,141,748 A | 8/1992 | Rizzo |
| 5,147,307 A | 9/1992 | Gluck |
| 5,147,631 A | 9/1992 | Glajch et al. |
| 5,162,430 A | 11/1992 | Rhee et al. |
| 5,163,896 A | 11/1992 | Suthanthiran et al. |
| 5,195,540 A | 3/1993 | Shiber |
| 5,197,482 A | 3/1993 | Rank et al. |
| 5,197,846 A | 3/1993 | Uno et al. |
| 5,199,441 A | 4/1993 | Hogle |
| 5,219,339 A | 6/1993 | Saito |
| 5,221,269 A | 6/1993 | Miller et al. |
| 5,231,615 A | 7/1993 | Endoh |
| 5,236,410 A | 8/1993 | Granov et al. |
| 5,242,759 A | 9/1993 | Hall |
| 5,250,026 A | 10/1993 | Ehrlich et al. |
| 5,271,961 A | 12/1993 | Mathiowitz et al. |
| 5,273,532 A | 12/1993 | Niezink et al. |
| 5,280,788 A | 1/1994 | Janes et al. |
| 5,281,197 A | 1/1994 | Arias et al. |
| 5,281,408 A | 1/1994 | Unger |
| 5,282,781 A | 2/1994 | Liprie |
| 5,284,479 A | 2/1994 | de Jong |
| 5,289,831 A | 3/1994 | Bosley |
| 5,320,613 A | 6/1994 | Houge et al. |
| 5,328,955 A | 7/1994 | Rhee et al. |
| 5,334,381 A | 8/1994 | Unger |
| 5,353,804 A | 10/1994 | Kornberg et al. |
| 5,354,623 A | 10/1994 | Hall |
| 5,358,514 A | 10/1994 | Schulman et al. |
| 5,366,756 A | 11/1994 | Chesterfield et al. |
| 5,368,030 A | 11/1994 | Zinreich et al. |
| 5,388,588 A | 2/1995 | Nabai et al. |
| 5,394,875 A | 3/1995 | Lewis et al. |
| 5,395,319 A | 3/1995 | Hirsch et al. |
| 5,409,004 A | 4/1995 | Sloan |
| 5,417,708 A | 5/1995 | Hall et al. |
| 5,422,730 A | 6/1995 | Barlow et al. |
| 5,425,366 A | 6/1995 | Reinhardt et al. |
| 5,431,639 A | 7/1995 | Shaw |
| 5,433,204 A | 7/1995 | Olson |
| 5,449,560 A | 9/1995 | Antheunis et al. |
| 5,451,406 A | 9/1995 | Lawin et al. |
| 5,460,182 A | 10/1995 | Goodman et al. |
| 5,469,847 A | 11/1995 | Zinreich et al. |
| 5,475,052 A | 12/1995 | Rhee et al. |
| 5,490,521 A | 2/1996 | Davis et al. |
| 5,494,030 A | 2/1996 | Swartz et al. |
| 5,499,989 A | 3/1996 | LaBash |
| 5,507,807 A | 4/1996 | Shippert |
| 5,508,021 A | 4/1996 | Grinstaff et al. |
| 5,514,085 A | 5/1996 | Yoon |
| 5,522,896 A | 6/1996 | Prescott |
| 5,538,726 A | 7/1996 | Order |
| 5,542,915 A | 8/1996 | Edwards et al. |
| 5,549,560 A | 8/1996 | Van de Wijdeven |
| RE35,391 E | 12/1996 | Brauman |
| 5,580,568 A | 12/1996 | Greff et al. |
| 5,585,112 A | 12/1996 | Unger et al. |
| 5,611,352 A | 3/1997 | Kobren et al. |
| 5,626,611 A | 5/1997 | Liu et al. |
| 5,628,781 A | 5/1997 | Williams et al. |
| 5,629,008 A | 5/1997 | Lee |
| 5,636,255 A | 6/1997 | Ellis |
| 5,643,246 A | 7/1997 | Leeb et al. |
| 5,646,146 A | 7/1997 | Faarup et al. |
| 5,667,767 A | 9/1997 | Greff et al. |
| 5,669,882 A | 9/1997 | Pyles |
| 5,673,841 A | 10/1997 | Schulze et al. |
| 5,676,146 A | 10/1997 | Scarborough |
| 5,676,925 A | 10/1997 | Klaveness et al. |
| 5,688,490 A | 11/1997 | Tournier et al. |
| 5,690,120 A | 11/1997 | Jacobsen et al. |
| 5,695,480 A | 12/1997 | Evans et al. |
| 5,702,128 A | 12/1997 | Maxim et al. |
| 5,702,716 A | 12/1997 | Dunn et al. |
| 5,747,060 A | 5/1998 | Sackler et al. |
| 5,762,903 A | 6/1998 | Park et al. |
| 5,769,086 A | 6/1998 | Ritchart et al. |
| 5,776,496 A | 7/1998 | Violante et al. |
| 5,779,647 A | 7/1998 | Chau et al. |
| 5,782,764 A | 7/1998 | Werne |
| 5,782,775 A | 7/1998 | Milliman et al. |
| 5,795,308 A | 8/1998 | Russin |
| 5,799,099 A | 8/1998 | Wang et al. |
| 5,800,362 A | 9/1998 | Kobren et al. |
| 5,800,389 A | 9/1998 | Burney et al. |
| 5,800,445 A | 9/1998 | Ratcliff et al. |
| 5,800,541 A | 9/1998 | Rhee et al. |
| 5,817,022 A | 10/1998 | Vesely |
| 5,820,918 A | 10/1998 | Ronan et al. |
| 5,821,184 A | 10/1998 | Haines et al. |
| 5,823,198 A | 10/1998 | Jones et al. |
| 5,824,042 A | 10/1998 | Lombardi et al. |
| 5,824,081 A | 10/1998 | Knapp et al. |
| 5,826,776 A | 10/1998 | Schulze et al. |
| 5,830,178 A | 11/1998 | Jones et al. |
| 5,842,477 A | 12/1998 | Naughton et al. |
| 5,842,999 A | 12/1998 | Pruitt et al. |
| 5,845,646 A | 12/1998 | Lemelson |
| 5,846,220 A | 12/1998 | Elsberry |
| 5,851,508 A | 12/1998 | Greff et al. |
| 5,853,366 A | 12/1998 | Dowlatshahi |
| 5,865,806 A | 2/1999 | Howell |
| 5,869,080 A | 2/1999 | McGregor et al. |
| 5,871,501 A | 2/1999 | Leschinsky et al. |
| 5,876,340 A | 3/1999 | Tu et al. |
| 5,879,357 A | 3/1999 | Heaton et al. |
| 5,891,558 A | 4/1999 | Bell et al. |

| | | | | | | |
|---|---|---|---|---|---|---|
| 5,897,507 | A | 4/1999 | Kortenbach et al. | 6,371,904 B1 | 4/2002 | Sirimanne et al. |
| 5,902,310 | A | 5/1999 | Foerster et al. | 6,394,965 B1 | 5/2002 | Klein |
| 5,911,705 | A | 6/1999 | Howell | 6,403,758 B1 | 6/2002 | Loomis |
| 5,916,164 | A | 6/1999 | Fitzpatrick et al. | 6,405,733 B1 | 6/2002 | Fogarty et al. |
| 5,921,933 | A | 7/1999 | Sarkis et al. | 6,409,742 B1 | 6/2002 | Fulton, III et al. |
| 5,922,024 | A | 7/1999 | Janzen et al. | 6,424,857 B1 | 7/2002 | Henrichs et al. |
| 5,928,626 | A | 7/1999 | Klaveness et al. | 6,425,903 B1 | 7/2002 | Voegele |
| 5,928,773 | A | 7/1999 | Andersen | 6,450,937 B1 | 9/2002 | Mercereau et al. |
| 5,941,439 | A | 8/1999 | Kammerer et al. | 6,450,938 B1 | 9/2002 | Miller |
| 5,941,890 | A | 8/1999 | Voegele et al. | 6,471,700 B1 | 10/2002 | Burbank et al. |
| 5,942,209 | A | 8/1999 | Leavitt et al. | 6,478,790 B2 | 11/2002 | Bardani |
| 5,948,425 | A | 9/1999 | Janzen et al. | 6,506,156 B1 | 1/2003 | Jones et al. |
| 5,954,670 | A | 9/1999 | Baker | 6,511,468 B1 | 1/2003 | Cragg et al. |
| 5,972,817 | A | 10/1999 | Haines et al. | 6,537,193 B1 | 3/2003 | Lennox |
| 5,989,265 | A | 11/1999 | Bouquet De La Joliniere et al. | 6,540,981 B2 | 4/2003 | Klaveness et al. |
| 6,015,541 | A | 1/2000 | Greff et al. | 6,544,185 B2 | 4/2003 | Montegrande |
| 6,030,333 | A | 2/2000 | Sioshansi et al. | 6,551,253 B2 | 4/2003 | Worm et al. |
| 6,053,925 | A | 4/2000 | Barnhart | 6,554,760 B2 | 4/2003 | Lamoureux et al. |
| 6,056,700 | A | 5/2000 | Burney et al. | 6,562,317 B2 | 5/2003 | Greff et al. |
| 6,066,122 | A | 5/2000 | Fisher | 6,564,806 B1 | 5/2003 | Fogarty et al. |
| 6,066,325 | A | 5/2000 | Wallace et al. | 6,565,551 B1 | 5/2003 | Jones et al. |
| 6,071,301 | A | 6/2000 | Cragg et al. | 6,575,888 B2 | 6/2003 | Zamora et al. |
| 6,071,310 | A | 6/2000 | Picha et al. | 6,575,991 B1 | 6/2003 | Chesbrough et al. |
| 6,071,496 | A | 6/2000 | Stein et al. | 6,605,047 B2 | 8/2003 | Zarins et al. |
| 6,096,065 | A | 8/2000 | Crowley | 6,610,026 B2 | 8/2003 | Cragg et al. |
| 6,096,070 | A | 8/2000 | Ragheb et al. | 6,613,002 B1 | 9/2003 | Clark et al. |
| 6,106,473 | A | 8/2000 | Violante et al. | 6,616,630 B1 | 9/2003 | Woehr et al. |
| 6,117,108 | A | 9/2000 | Woehr et al. | 6,626,850 B1 | 9/2003 | Chau et al. |
| 6,120,536 | A | 9/2000 | Ding et al. | 6,628,982 B1 | 9/2003 | Thomas et al. |
| 6,142,955 | A | 11/2000 | Farascioni et al. | 6,636,758 B2 | 10/2003 | Sanchez et al. |
| 6,159,445 | A | 12/2000 | Klaveness et al. | 6,638,234 B2 | 10/2003 | Burbank et al. |
| 6,161,034 | A | 12/2000 | Burbank et al. | 6,638,308 B2 | 10/2003 | Corbitt, Jr. et al. |
| 6,162,192 | A | 12/2000 | Cragg et al. | 6,652,442 B2 | 11/2003 | Gatto |
| 6,173,715 | B1 | 1/2001 | Sinanan et al. | 6,656,192 B2 | 12/2003 | Espositio et al. |
| 6,174,330 | B1 | 1/2001 | Stinson | 6,699,205 B2 | 3/2004 | Fulton, III et al. |
| 6,177,062 | B1 | 1/2001 | Stein et al. | 6,712,774 B2 | 3/2004 | Voegele et al. |
| 6,181,960 | B1 | 1/2001 | Jensen et al. | 6,712,836 B1 | 3/2004 | Berg et al. |
| 6,183,497 | B1 | 2/2001 | Sing et al. | 6,716,444 B1 | 4/2004 | Castro et al. |
| 6,190,350 | B1 | 2/2001 | Davis et al. | 6,725,083 B1 | 4/2004 | Burbank et al. |
| 6,190,353 | B1 | 2/2001 | Makower et al. | 6,730,042 B2 | 5/2004 | Fulton et al. |
| 6,200,258 | B1 | 3/2001 | Slater et al. | 6,730,044 B2 | 5/2004 | Stephens et al. |
| 6,203,524 | B1 | 3/2001 | Burney et al. | 6,746,661 B2 | 6/2004 | Kaplan |
| 6,203,568 | B1 | 3/2001 | Lombardi et al. | 6,746,773 B2 | 6/2004 | Llanos et al. |
| 6,213,957 | B1 | 4/2001 | Milliman et al. | 6,752,154 B2 | 6/2004 | Fogarty et al. |
| 6,214,045 | B1 | 4/2001 | Corbitt, Jr. et al. | 6,766,186 B1 | 7/2004 | Hoyns et al. |
| 6,214,315 | B1 | 4/2001 | Greff et al. | 6,774,278 B1 | 8/2004 | Ragheb et al. |
| 6,220,248 | B1 | 4/2001 | Voegele et al. | 6,780,179 B2 | 8/2004 | Lee et al. |
| 6,224,630 | B1 | 5/2001 | Bao et al. | 6,824,507 B2 | 11/2004 | Miller |
| 6,228,049 | B1 | 5/2001 | Schroeder et al. | 6,824,527 B2 | 11/2004 | Gollobin |
| 6,228,055 | B1 | 5/2001 | Foerster et al. | 6,846,320 B2 | 1/2005 | Ashby et al. |
| 6,231,615 | B1 | 5/2001 | Preissman | 6,862,470 B2 | 3/2005 | Burbank et al. |
| 6,234,177 | B1 | 5/2001 | Barsch | 6,863,685 B2 | 3/2005 | Davila et al. |
| 6,241,687 | B1 | 6/2001 | Voegele et al. | 6,899,731 B2 | 5/2005 | Li et al. |
| 6,241,734 | B1 | 6/2001 | Scribner et al. | 6,918,927 B2 | 7/2005 | Bates et al. |
| 6,251,418 | B1 | 6/2001 | Ahern et al. | 6,936,014 B2 | 8/2005 | Vetter et al. |
| 6,261,243 | B1 | 7/2001 | Burney et al. | 6,939,318 B2 | 9/2005 | Stenzel |
| 6,261,302 | B1 | 7/2001 | Voegele et al. | 6,945,973 B2 | 9/2005 | Bray |
| 6,264,917 | B1 | 7/2001 | Klaveness et al. | 6,951,564 B2 | 10/2005 | Espositio et al. |
| 6,270,464 | B1 | 8/2001 | Fulton, III et al. | 6,992,233 B2 | 1/2006 | Drake et al. |
| 6,270,472 | B1 | 8/2001 | Antaki et al. | 6,994,712 B1 | 2/2006 | Fisher et al. |
| 6,287,278 | B1 | 9/2001 | Woehr et al. | 7,001,341 B2 | 2/2006 | Gellman et al. |
| 6,287,332 | B1 | 9/2001 | Bolz et al. | 7,008,382 B2 | 3/2006 | Adams et al. |
| 6,289,229 | B1 | 9/2001 | Crowley | 7,014,610 B2 | 3/2006 | Koulik |
| 6,306,154 | B1 | 10/2001 | Hudson et al. | 7,025,765 B2 | 4/2006 | Balbierz et al. |
| 6,312,429 | B1 | 11/2001 | Burbank et al. | 7,044,957 B2 | 5/2006 | Foerster et al. |
| 6,316,522 | B1 | 11/2001 | Loomis et al. | 7,083,576 B2 | 8/2006 | Zarins et al. |
| 6,335,029 | B1 | 1/2002 | Kamath et al. | 7,125,397 B2 | 10/2006 | Woehr et al. |
| 6,336,904 | B1 | 1/2002 | Nikolchev | 7,172,549 B2 | 2/2007 | Slater et al. |
| 6,340,367 | B1 | 1/2002 | Stinson et al. | 7,214,211 B2 | 5/2007 | Woehr et al. |
| 6,343,227 | B1 | 1/2002 | Crowley | 7,229,417 B2 | 6/2007 | Foerster et al. |
| 6,347,240 | B1 | 2/2002 | Foley et al. | 7,236,816 B2 | 6/2007 | Kumar et al. |
| 6,347,241 | B2 | 2/2002 | Burbank et al. | 7,264,613 B2 | 9/2007 | Woehr et al. |
| 6,350,244 | B1 | 2/2002 | Fisher | 7,294,118 B2 | 11/2007 | Saulenas et al. |
| 6,350,274 | B1 | 2/2002 | Li | 7,297,725 B2 | 11/2007 | Winterton et al. |
| 6,354,989 | B1 | 3/2002 | Nudeshima | 7,329,402 B2 | 2/2008 | Unger et al. |
| 6,356,112 | B1 | 3/2002 | Tran et al. | 7,416,533 B2 | 8/2008 | Gellman et al. |
| 6,356,782 | B1 | 3/2002 | Sirimanne et al. | 7,424,320 B2 | 9/2008 | Chesbrough et al. |
| 6,358,217 | B1 | 3/2002 | Bourassa | 7,449,000 B2 | 11/2008 | Adams et al. |
| 6,363,940 | B1 | 4/2002 | Krag | 7,527,610 B2 | 5/2009 | Erickson |

| | | |
|---|---|---|
| 7,534,452 B2 | 5/2009 | Chernomorsky et al. |
| 7,569,065 B2 | 8/2009 | Chesbrough et al. |
| 7,577,473 B2 | 8/2009 | Davis et al. |
| 7,637,948 B2 | 12/2009 | Corbitt, Jr. |
| 7,651,505 B2 | 1/2010 | Lubock et al. |
| 7,819,820 B2 | 10/2010 | Field et al. |
| 7,877,133 B2 | 1/2011 | Burbank et al. |
| 7,945,307 B2 | 5/2011 | Lubock et al. |
| 2001/0006616 A1 | 7/2001 | Leavitt et al. |
| 2002/0004060 A1 | 1/2002 | Heublein et al. |
| 2002/0016625 A1 | 2/2002 | Falotico et al. |
| 2002/0022883 A1 | 2/2002 | Burg |
| 2002/0026201 A1 | 2/2002 | Foerster et al. |
| 2002/0035324 A1 | 3/2002 | Sirimanne et al. |
| 2002/0045842 A1 | 4/2002 | Van Bladel et al. |
| 2002/0052572 A1 | 5/2002 | Franco et al. |
| 2002/0055731 A1 | 5/2002 | Atala et al. |
| 2002/0058868 A1 | 5/2002 | Hoshino et al. |
| 2002/0058882 A1 | 5/2002 | Fulton, III et al. |
| 2002/0077687 A1 | 6/2002 | Ahn |
| 2002/0082519 A1 | 6/2002 | Miller et al. |
| 2002/0082682 A1 | 6/2002 | Barclay et al. |
| 2002/0082683 A1 | 6/2002 | Stinson et al. |
| 2002/0095204 A1 | 7/2002 | Thompson et al. |
| 2002/0095205 A1 | 7/2002 | Edwin et al. |
| 2002/0107437 A1 | 8/2002 | Sirimanne et al. |
| 2002/0133148 A1 | 9/2002 | Daniel et al. |
| 2002/0143359 A1 | 10/2002 | Fulton, III et al. |
| 2002/0165608 A1 | 11/2002 | Llanos et al. |
| 2002/0193815 A1 | 12/2002 | Foerster et al. |
| 2002/0193867 A1 | 12/2002 | Gladdish, Jr. et al. |
| 2003/0036803 A1 | 2/2003 | McGhan |
| 2003/0051735 A1 | 3/2003 | Pavcnik et al. |
| 2003/0116806 A1 | 6/2003 | Kato |
| 2003/0165478 A1 | 9/2003 | Sokoll |
| 2003/0191355 A1 | 10/2003 | Ferguson |
| 2003/0199887 A1 | 10/2003 | Ferrera et al. |
| 2003/0225420 A1 | 12/2003 | Wardle |
| 2003/0236573 A1 | 12/2003 | Evans et al. |
| 2004/0001841 A1 | 1/2004 | Nagavarapu et al. |
| 2004/0002650 A1 | 1/2004 | Mandrusov et al. |
| 2004/0016195 A1 | 1/2004 | Archuleta |
| 2004/0024304 A1 | 2/2004 | Foerster et al. |
| 2004/0059341 A1 | 3/2004 | Gellman et al. |
| 2004/0073107 A1 | 4/2004 | Sioshansi et al. |
| 2004/0073284 A1 | 4/2004 | Bates et al. |
| 2004/0097981 A1 | 5/2004 | Selis |
| 2004/0101479 A1 | 5/2004 | Burbank et al. |
| 2004/0101548 A1 | 5/2004 | Pendharkar |
| 2004/0106891 A1 | 6/2004 | Langan et al. |
| 2004/0116802 A1 | 6/2004 | Jessop et al. |
| 2004/0124105 A1 | 7/2004 | Seiler et al. |
| 2004/0127765 A1 | 7/2004 | Seiler et al. |
| 2004/0133124 A1 | 7/2004 | Bates et al. |
| 2004/0162574 A1 | 8/2004 | Viola |
| 2004/0167619 A1 | 8/2004 | Case et al. |
| 2004/0204660 A1 | 10/2004 | Fulton et al. |
| 2004/0210208 A1 | 10/2004 | Paul et al. |
| 2004/0213756 A1 | 10/2004 | Michal et al. |
| 2004/0236212 A1 | 11/2004 | Jones et al. |
| 2004/0236213 A1 | 11/2004 | Jones et al. |
| 2005/0020916 A1 | 1/2005 | MacFarlane et al. |
| 2005/0033157 A1 | 2/2005 | Klein et al. |
| 2005/0033195 A1 | 2/2005 | Fulton et al. |
| 2005/0036946 A1 | 2/2005 | Pathak et al. |
| 2005/0045192 A1 | 3/2005 | Fulton et al. |
| 2005/0059887 A1 | 3/2005 | Mostafavi et al. |
| 2005/0059888 A1 | 3/2005 | Sirimanne et al. |
| 2005/0065354 A1 | 3/2005 | Roberts |
| 2005/0065453 A1 | 3/2005 | Shabaz et al. |
| 2005/0080337 A1 | 4/2005 | Sirimanne et al. |
| 2005/0080339 A1 | 4/2005 | Sirimanne et al. |
| 2005/0085724 A1 | 4/2005 | Sirimanne et al. |
| 2005/0100580 A1 | 5/2005 | Osborne et al. |
| 2005/0113659 A1 | 5/2005 | Pothier et al. |
| 2005/0119562 A1 | 6/2005 | Jones et al. |
| 2005/0143650 A1 | 6/2005 | Winkel |
| 2005/0165305 A1 | 7/2005 | Foerster et al. |
| 2005/0175657 A1 | 8/2005 | Hunter et al. |
| 2005/0181007 A1 | 8/2005 | Hunter et al. |
| 2005/0208122 A1 | 9/2005 | Allen et al. |
| 2005/0234336 A1 | 10/2005 | Beckman et al. |
| 2005/0268922 A1 | 12/2005 | Conrad et al. |
| 2005/0273002 A1 | 12/2005 | Goosen et al. |
| 2005/0277871 A1 | 12/2005 | Selis |
| 2006/0004440 A1 | 1/2006 | Stinson |
| 2006/0009800 A1 | 1/2006 | Christianson et al. |
| 2006/0036158 A1 | 2/2006 | Field et al. |
| 2006/0036159 A1 | 2/2006 | Sirimanne et al. |
| 2006/0074443 A1 | 4/2006 | Foerster et al. |
| 2006/0079770 A1 | 4/2006 | Sirimanne et al. |
| 2006/0079805 A1 | 4/2006 | Miller et al. |
| 2006/0079829 A1 | 4/2006 | Fulton et al. |
| 2006/0079888 A1 | 4/2006 | Mulier et al. |
| 2006/0122503 A1 | 6/2006 | Burbank et al. |
| 2006/0155190 A1 | 7/2006 | Burbank et al. |
| 2006/0173280 A1 | 8/2006 | Goosen et al. |
| 2006/0173296 A1 | 8/2006 | Miller et al. |
| 2006/0177379 A1 | 8/2006 | Asgari |
| 2006/0217635 A1 | 9/2006 | McCombs et al. |
| 2006/0235298 A1 | 10/2006 | Kotmel et al. |
| 2006/0241385 A1 | 10/2006 | Dietz |
| 2006/0241411 A1 | 10/2006 | Field et al. |
| 2006/0292690 A1 | 12/2006 | Liu et al. |
| 2007/0021642 A1 | 1/2007 | Lamoureux et al. |
| 2007/0038145 A1 | 2/2007 | Field |
| 2007/0057794 A1 | 3/2007 | Gisselberg et al. |
| 2007/0083132 A1 | 4/2007 | Sharrow |
| 2007/0087026 A1 | 4/2007 | Field |
| 2007/0106152 A1 | 5/2007 | Kantrowitz et al. |
| 2007/0135711 A1 | 6/2007 | Chernomorsky et al. |
| 2007/0142725 A1 | 6/2007 | Hardin et al. |
| 2007/0167736 A1 | 7/2007 | Dietz et al. |
| 2007/0167749 A1 | 7/2007 | Yarnall et al. |
| 2007/0239118 A1 | 10/2007 | Ono et al. |
| 2007/0287933 A1 | 12/2007 | Phan et al. |
| 2008/0039819 A1 | 2/2008 | Jones et al. |
| 2008/0097199 A1 | 4/2008 | Mullen |
| 2008/0188768 A1 | 8/2008 | Zarins et al. |
| 2008/0249436 A1 | 10/2008 | Darr |
| 2008/0269638 A1 | 10/2008 | Cooke et al. |
| 2008/0294039 A1 | 11/2008 | Jones et al. |
| 2009/0000629 A1 | 1/2009 | Hornscheidt et al. |
| 2009/0024225 A1 | 1/2009 | Stubbs |
| 2009/0069713 A1 | 3/2009 | Adams et al. |
| 2009/0076484 A1 | 3/2009 | Fukaya |
| 2009/0131825 A1 | 5/2009 | Burbank et al. |
| 2009/0171198 A1 | 7/2009 | Jones et al. |
| 2009/0216118 A1 | 8/2009 | Jones et al. |
| 2010/0010341 A1 | 1/2010 | Talpade et al. |
| 2010/0030072 A1 | 2/2010 | Casanova et al. |
| 2010/0030149 A1 | 2/2010 | Carr, Jr. |

FOREIGN PATENT DOCUMENTS

| | | |
|---|---|---|
| EP | 0255123 A2 | 2/1988 |
| EP | 0292936 A2 | 11/1988 |
| EP | 0458745 A1 | 11/1991 |
| EP | 0475077 A2 | 3/1992 |
| EP | 0552924 A1 | 7/1993 |
| EP | 0769281 A2 | 4/1997 |
| EP | 1114618 A2 | 7/2001 |
| EP | 1163888 A1 | 12/2001 |
| EP | 1281416 A2 | 6/2002 |
| EP | 1364628 A1 | 11/2003 |
| EP | 1493451 A1 | 1/2005 |
| EP | 1767167 A2 | 3/2007 |
| FR | 2646674 A3 | 11/1990 |
| GB | 708148 | 4/1954 |
| JP | 2131757 A | 5/1990 |
| WO | 8906978 A1 | 8/1989 |
| WO | 9112823 A1 | 9/1991 |
| WO | 9314712 A1 | 8/1993 |
| WO | 9317671 A1 | 9/1993 |
| WO | 9317718 A1 | 9/1993 |
| WO | 9416647 A1 | 8/1994 |
| WO | 9507057 A1 | 3/1995 |
| WO | 9806346 A1 | 2/1998 |
| WO | 9908607 A1 | 2/1999 |

| | | | |
|---|---|---|---|
| WO | 9935966 A1 | 7/1999 |
| WO | 9951143 A1 | 10/1999 |
| WO | 0023124 A1 | 4/2000 |
| WO | 0024332 A1 | 5/2000 |
| WO | 0028554 A1 | 5/2000 |
| WO | 0054689 A1 | 9/2000 |
| WO | 0108578 A1 | 2/2001 |
| WO | 0170114 A1 | 9/2001 |
| WO | 0207786 A2 | 1/2002 |
| WO | 03000308 A1 | 1/2003 |
| WO | 2004045444 A2 | 6/2004 |
| WO | 2005013832 A1 | 2/2005 |
| WO | 2005089664 A1 | 9/2005 |
| WO | 2006012630 A2 | 2/2006 |
| WO | 2006056739 A2 | 6/2006 |
| WO | 2006097331 A2 | 9/2006 |
| WO | 2006105353 A2 | 10/2006 |
| WO | 2007069105 A2 | 6/2007 |
| WO | 2008077081 A2 | 6/2008 |

OTHER PUBLICATIONS

Fucci, V., et al., "Large Bowel Transit Times Using Radioopaque Markers in Normal Cats", J. of Am. Animal Hospital Assn., Nov.-Dec. 1995 31 (6) 473-477.

Schindlbeck, N.E., et al., "Measurement of Colon Transit Time", J. of Gastroenterology, No. 28, pp. 399-404, 1990.

Shiga, et al., Preparation of Poly(D, L-lactide) and Copoly(lactide-glycolide) Microspheres of Uniform Size, J. Pharm. Pharmacol. 1996 48:891-895.

Eiselt, P. et al, "Development of Technologies Aiding Large—Tissue Engineering", Biotechnol. Prog., vol. 14, No. 1, pp. 134-140, 1998.

Meuris, Bart, "Calcification of Aortic Wall Tissue in Prosthetic Heart Valves: Initiation, Influencing Factors and Strategies Towards Prevention", Thesis, 2007, pp. 21-36, Leuven University Press; Leuven, Belgium.

Press release for Biopsys Ethicon Endo-Surgery (Europe) GmbH; The Mammotome Vacuum Biopsy System. From: http://www.medicine-news.com/articles/devices/mammotome.html. 3 pages.

Johnson & Johnson: Breast Biopsy (minimally invasive): Surgical Technique: Steps in the Mamotome Surgical Procedure. From http://www.jnjgateway.com. 3 pages.

Johnson & Johnson: New Minimally Invasive Breast Biopsy Device Receives Marketing Clearance in Canada; Aug. 6, 1999. From http://www.jnjgateway.com. 4 pages.

Johnson & Johnson: Mammotome Hand Held Receives FDA Marketing Clearance for Minimally Invasive Breast Biopises; Sep. 1, 1999. From From http://www.jnjgateway.com. 5 pages.

Johnson & Johnson: The Mammotome Breast Biopsy System. From: http://www.breastcareinfo.com/aboutm.htm. 6 pages.

Cook Incorporated: Emoblization and Occlusion. From: www.cookgroup.com 6 pages.

Liberman, Laura, et al. Percutaneous Removal of Malignant Mammographic Lesions at Stereotactic Vacuum-assisted Biopsy. From: The Departments of Radiology, Pathology, and Surgery. Memorial Sloan-Kettering Cancer Center. From the 1997 RSNA scientific assembly. vol. 206, No. 3. pp. 711-715.

Fajardo, Laurie, et al., "Placement of Endovascular Embolization Microcoils to Localize the Site of Breast Lesions Removed at Stereotactic Core Biopsy", Radiology, Jan. 1998, pp. 275-278, vol. 206—No. 1.

H. J. Gent, M.D., et al., Stereotaxic Needle Localization and Cytological Diagnosis of Occult Breast Lesions, Annals of Surgery, Nov. 1986, pp. 580-584, vol. 204—No. 5.

BREAST MARKER

PRIORITY

This application is a continuation of U.S. patent application Ser. No. 12/446,644, filed Apr. 22, 2009, now U.S. Pat. No. 8,064,987, which is a U.S. National Stage of International Application No. PCT/US2007/081399, filed Oct. 15, 2007, which claims the benefit of priority to U.S. Provisional Patent Application No. 60/853,633, filed Oct. 23, 2006, which is incorporated by reference into this application as if fully set forth herein.

BACKGROUND

It is often desirable to mark tissue with a marker so that it can later be identified. For example, tissue may be sampled by performing a biopsy to remove a small portion of the tissue. If the biopsy site is marked, the marker may later be used to guide a doctor or health care professional in returning to the site of the biopsy, should further medical procedures need to be performed at this site. For example, tissue (including small masses or microcalcifications) is sometimes completely removed by procedures such as stereotactic core biopsy. Often during these procedures, a metal clip is employed through the biopsy needle to mark the target. Should another procedure be required in the same area (e.g. a further excision or biopsy), the metal clip acts as a marker to aid in re-identification of the target or target region. The marker may also be used to confirm that the biopsied site matches the intended target.

Unfortunately, there are many problems with currently available markers such as the metal clips mentioned above. In particular, markers such as metal clips may move (or migrate) from the correct or initial position. Furthermore, the size and shape of these metal clips or other markers is limited because they must typically fit within the small diameter of a delivery needle. Finally, there may be problems identifying the marker once it has been inserted.

Migration of tissue markers is a well-described phenomenon, which can cause serious problems with patient treatment. Migration may occur immediately after insertion, or it may occur some time after insertion, and may have many causes. One common cause of clip migration occurs when the tissue (e.g., breast tissue) re-expands after compression or pressure on the tissue is released, for example, when the biopsy procedure is completed. This may be referred to as the "accordion effect." Markers may also be displaced after being inserted into the tissue by formation of a hematoma, because the marker (particularly smaller markers) may "float" within the hematoma.

Most currently available tissue markers are also limited to visualization (or localization) by a single imaging modality. For example, metal clip markers may be radioopaque and therefore visible by X-ray based modalities, but may not be visualized by ultrasound or other modalities. Furthermore, imaging of a tissue marker may also be limited by the size or shape of the marker, because the size and shape of most currently available markers are constrained by the insertion mechanism. For example, markers that are inserted through a biopsy needle generally have a cross-sectional dimension that is smaller than the diameter of the biopsy needle even after they have been inserted into the body.

Exemplary tissue markers have been described in U.S. Pat. No. 6,228,055 to Foerster et al., U.S. Pat. No. 6,261,243 to Burney et al., U.S. Pat. No. 6,350,244 to Fisher, U.S. Pat. No. 6,234,177 to Barsch, and U.S. Pat. No. 6,371,904 to Sirimanne et al. Each of these references is incorporated in its entirety herein. However, none of these devices adequately addresses all of the concerns described above.

Applicants have recognized that it would be desirable to provide a relatively large tissue marker that is deliverable in a smaller profile sheath, embodiments of which are described herein along with methods of making same.

SUMMARY

Described herein are tissue markers, systems for marking tissue, and methods of using tissue markers. In general, any of the tissue markers described herein may be used to mark any appropriate tissue, including breast tissue.

Accordingly, in one embodiment, a tissue marker includes a body with a first surface and a second surface and a plurality of coupling sites. The tissue marker also includes a plurality of elongate members. At least one of the body and/or one or more of the elongate members includes a remotely visible material. The first and second surfaces each have a minor diameter and a major diameter, and the major diameter is larger than the minor diameter. Each elongate member extends from a coupling site on at least one of the first and second surfaces. One or more of the elongate members are configured to be positioned with respect to the body in a delivery configuration and a deployed configuration. The deployed configuration is different from the delivery configuration.

Also described herein are delivery systems. In one embodiment, a delivery system includes a sheath having a lumen, a pusher element disposed in the lumen, and a tissue marker disposed in the lumen distal of the pusher element. The tissue marker includes a body having a first surface and a second surface and a plurality of coupling sites. The tissue marker also includes a plurality of elongate members, and at least one of the body and/or one or more of the elongate members includes a remotely visible material. The first and second surfaces each have a minor diameter and a major diameter. The major diameter is larger than the minor diameter. Each elongate member extends from a coupling site on at least one of the first and second surfaces. One or more of the elongate members is configured to be positioned with respect to the body in a delivery configuration and a deployed configuration; the deployed configured is different from the delivery configuration.

Also described herein are methods of delivering a tissue marker to a tissue site. In one embodiment, the method includes inserting a sheath (having a tissue marker disposed in a delivery configuration therein) into a tissue site, and releasing the tissue marker from the sheath. The tissue marker may have a body including a first surface and a second surface and a plurality of coupling sites, and a plurality of elongate members, where each elongate member extending from a coupling site on at least one of the first and second surfaces. The first and second surfaces may have a minor diameter and a major diameter (where the major diameter is larger than the minor diameter). One or more of the elongate members may be configured to be positioned with respect to the body in a delivery configuration and a deployed configuration, where the deployed configuration is different from the delivery configuration. At least one of the body and/or one or more of the elongate members includes a remotely visible material.

These and other embodiments, features and advantages will become more apparent to those skilled in the art when taken with reference to the following more detailed descrip-

DETAILED DESCRIPTION

Figure 1A:
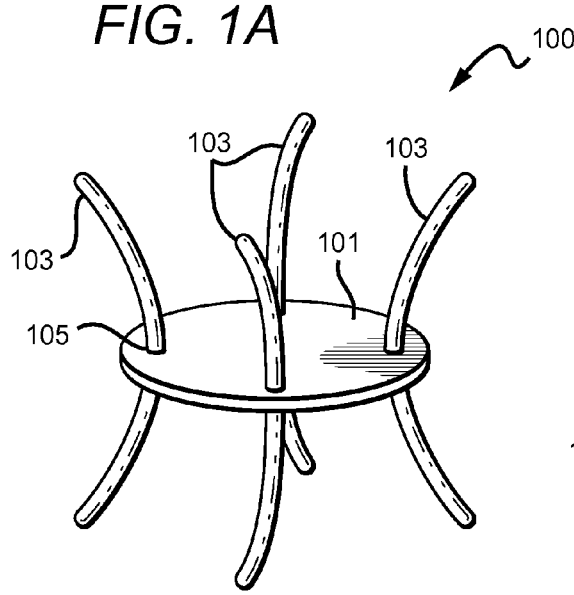
FIGS. 1A and 1B are perspective and side views of one embodiment of a tissue marker.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. Also, as used herein, the terms "patient", "host" and "subject" refer to any human or animal subject and are not intended to limit the systems or methods to human use, although use of the subject invention in a human patient represents a preferred embodiment.

The tissue marker described herein may include one or more members or regions (e.g., body region, elongate members, coupling sites) made of a bioabsorbable/bioresorbable material. One suitable bioabsorbable material can be one or more of a metal alloy shown and described in U.S. Pat. No. 6,287,332, or the metal alloy shown and described in U.S. Patent Application Publication No. 2002/0004060, each of which is incorporated by reference in its entirety into this application. Preferably, the metallic bioabsorbable material is selected from a first group consisting essentially of: magnesium, titanium, zirconium, niobium, tantalum, zinc, silicon, and combinations thereof. Also provided are mixtures and alloys of metallic bioabsorbable materials, including those selected from the first group. Various alloys of the materials in the first group can also be used as a metallic bioabsorbable material, such as a zinc-titanium alloy, for example, as discussed in U.S. Pat. No. 6,287,332 to Bolz et al., which is incorporated by reference in its entirety into this application.

The physical properties of the alloy can be controlled by selecting the metallic bioabsorbable material, or forming alloys of two or more metallic bioabsorbable materials. For example, the percentage by weight of titanium can be in the range of about 0.1% to about 1%, which can reduce the brittle quality of crystalline zinc. Without being bound to theory, it is believed that the addition of titanium leads to the formation of a Zn15Ti phase. In another embodiment, gold can be added to the zinc-titanium alloy at a percentage by weight of about 0.1% to about 2%, which is believed to result in a further reduction of the grain size when the material cures and further improving the tensile strength of the material.

In some embodiments, the metallic bioabsorbable material can be an alloy of materials from the first group and a material selected from a second group consisting essentially of: lithium, sodium, potassium, calcium, iron, manganese, and combinations thereof. The metallic bioabsorbable material from the first group can form a protective oxide or passivation coating upon exposure to blood or interstitial fluid. The material from the second group is preferably soluble in blood or interstitial fluid to promote the dissolution of the oxide coating. Also provided are mixtures and alloys of metallic bioabsorbable materials, including those selected from the second group and combinations of materials from the first group and the second group.

Briefly, the combination of metal materials can be a metal alloy, the selection of the alloy constituents (as explained in detail below) serving to attain the prerequisite of biocompatible decomposition. Consequently, the metal alloy may consist of a combination of material that will decompose in the body comparatively rapidly while forming harmless constituents. Such alloy may include a component A which covers itself with a protective oxide coating. This component A is selected from one or several metals of the group of magnesium, titanium, zirconium, niobium, tantalum, zinc, silicon, or combinations thereof. For uniform dissolution of the mentioned oxide coat to be attained, a component B is added to the alloy, possessing sufficient solubility in blood or interstitial fluid, such as lithium sodium, potassium, calcium, iron or manganese. The corrosion rate is adjusted by way of the composition so that gases, such as hydrogen, which evolve during the corrosion of lithium, sodium, potassium, magnesium, calcium or zinc, dissolve physically and essentially not forming any macroscopic gas bubbles. Other alloys can be utilized such as, for example, alloy of lithium and magnesium in the ratio of about 60:40; a sodium-magnesium alloy; a zinc-titanium alloy—the percentage by weight of which is in the range of about 0.1% to about 1% with the gold being optionally added at a percentage by weight of about 0.1% to about 2%. Further details relating to these metallic bioabsorbable materials are found in U.S. Pat. No. 6,287,332 to Bolz et al.

Other materials for one or more members of the tissue marker as described herein can include biodegradable polymers including shape memory polymers, such as, for example, polylactic acid, i.e., PLA, polyglycolic acid, i.e., PGA, polydioxanone, i.e., PDS, polyhydroxybutyrate, i.e., PHB, polyhydroxyvalerate, i.e., PHV and copolymers or a combination of PHB and PHV (available commercially as Biopol®), polycaprolactone (available as Capronor®), polyanhydrides (aliphatic polyanhydrides in the back bone or side chains or aromatic polyanhydrides with benzene in the side chain), polyorthoesters, polyaminoacids (e.g., poly-L-lysine, polyglutamic acid), pseudo-polyaminoacids (e.g., with back bone of polyaminoacids altered), polycyanocrylates, or polyphosphazenes.

As used herein, the term "bioresorbable" or "bioabsorbable" includes a suitable biocompatible material, mixture of materials or partial components of materials being degraded into other generally non-toxic materials by an agent present in biological tissue (i.e., being bio-degradable via a suitable mechanism, such as, for example, hydrolysis) or being removed by cellular activity (i.e., bioresorption, bioabsorption, or bioresorbable), by bulk or surface degradation (i.e., bioerosion such as, for example, by utilizing a water insoluble polymer that is soluble in water upon contact with biological tissue or fluid), or a combination of one or more of the biodegradable, bioerodable, or bioresorbable material noted above.

As mentioned above, the tissue markers described herein may be used to mark any appropriate tissue. In particular, the tissue marker may be configured as a breast tissue marker. For the sake of convenience, the description provided below is sectioned into a description of tissue markers (including breast tissue markers), inserters for inserting a tissue markers (including systems for inserting tissue markers), and methods of inserting and visualizing these tissue markers. Features included in the description from any of the sections below may be applied to any of the other sections. For example, features of the tissue markers described herein may be applied to the systems and methods for using such tissue markers.

In general, the tissue markers described herein include a body having one or more coupling sites that couple to one or more elongate members. At least one region of either the body and/or one or more elongate member may include a remotely visible material that aids in visualization of the tissue marker. The tissue marker, and particularly an elongate member of the tissue marker, may include one or more attachment members configured to help secure the marker in the tissue. The tissue marker generally has a delivery configuration and a deployed configuration, and may change from the delivery configuration (either automatically or by some active mechanism) into the deployed configuration after being inserted into a target tissue site.

Figure 1B:
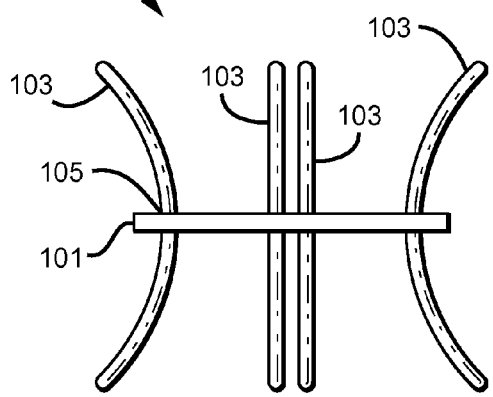

FIGS. 1A and 1B illustrate one embodiment of a tissue marker. FIG. 1A shows a perspective view of a tissue marker. This tissue marker includes a body 101 (also referred to as a body region) and a plurality of elongate members 103 attached to the body region through attachment members 105. The body, elongate members, and attachment region are described more fully below. FIG. 1B shows a side view of the tissue marker shown in FIG. 1A.

The body of the tissue marker may form the core region of the marker. In some embodiments the body is a constant shape. In other embodiments, the body may change shape (e.g., between a deployed and a delivery configuration). The body of the tissue markers described herein may have any appropriate shape, but particularly shapes having at least a first surface and a second surface, where the first and second surfaces have a major diameter and a minor diameter. As used herein, the "surfaces" of the body may be any appropriate surfaces. For example a surface of the body of the tissue marker may include flat or curved surfaces, and include smooth or irregular (e.g., rough) surfaces, continuous or interrupted surfaces, stiff or flexible surfaces, or the like. As used herein, the term "diameter" may mean the distance across a surface. A diameter, including a major or minor diameter, may be measured across a surface in a straight or a curved line. In general, the major diameter of a surface is the largest diameter across the surface, and the minor diameter of the surface is the smallest diameter measured across the surface. The major diameter of the surface of a tissue marker is typically larger than the minor diameter of the surface of a tissue marker. For example, in one embodiment, the length of the major diameter may be approximately 1.1×, 1.2×, 1.5×, 2×, 3×, 4×, 5×, 10×, etc. the length of the minor diameter. In some embodiments, the major and minor diameter may be approximately equivalent to one another. Although the three-dimensional shape of a surface of the tissue marker body may change (e.g., the tissue marker body may bend or flex), the major and/or minor diameters may remain relatively the same. In some embodiments, the major and minor diameter of the tissue marker body may change.

As mentioned, a surface of the body of the breast marker may be planar (e.g., flat) or curved. The surface may be generally oval, triangular, rectangular, polyhedral, or some combination of these shapes. In general, the body of the breast measurement device comprises at least two surfaces which may connect to each other directly (e.g., at an edge) or may be connected via one or more side walls. For example, the body of a breast marker may have a generally flattened oval shape having a first (e.g., upper) surface and a second (e.g., lower) surface. In some embodiments the first and second surfaces do not meet at a defined edge.

In general, the body of the breast marker includes at least two surfaces, and these surfaces may be part of the overall structure of the breast marker body. For example, the body a may be generally flattened (e.g., disk-shaped or the like), or rounded. In some embodiments, the body may be flexible so that the shape of the body may change. For example, the body may have an expanded or relaxed deployed configuration and a compressed delivery configuration. In one embodiment, at least a portion of the body is made of a flexible material that can be bent to permit the body or tissue marker to assume a delivery configuration that has a smaller profile than a relaxed (unbent) or deployed configuration, as described in further detail below. Although many of the embodiments of the tissue marker body described herein are solid shapes, other shapes may be useful as body shapes. For example, the body may be a scaffold, or may include connecting regions that help connect different regions of the body.

The body of the tissue marker may be made of any appropriate material, or combination of materials, particularly including the metal and polymeric materials (e.g., the bioabsorbable/bioresorbable material) described above. The body may be made of a single material or combination of materials, or it may have different regions that comprise different materials. In some embodiments, one or more surfaces of the tissue marker body may be coated or partially coated with a material that aids in delivery of the device. For example, the body may have a lubricious coating. Other coatings may include bioactive coatings (e.g., drug eluting coatings, coatings to encourage or inhibit tissue ingrowth, or the like), visualization coatings (e.g., radiopaque coatings, florescent coatings, etc.), protective coatings (e.g., wax coatings, polymeric coatings, etc.). The tissue marker body may also include regions comprising materials that are bioactive (e.g., configured to be released from the tissue marker over time), or for visualization. For example, the tissue marker may include one or more internal regions (e.g., a core) made of any material that may be visualized remotely, after the tissue marker has been implanted in to body, or to help visualize the tissue marker after it has been implanted.

Figure 2A:
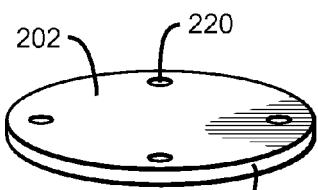
FIGS. 2A-2C are perspective views of various exemplary tissue marker body regions.
Figure 2B:
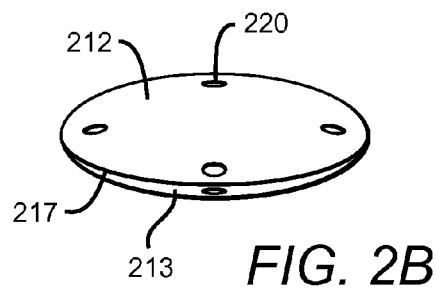
Figure 2C:
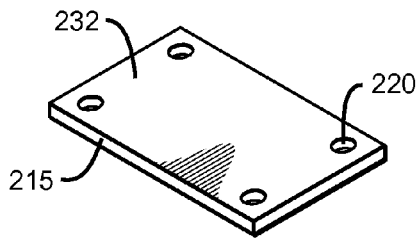
Figure 2D:
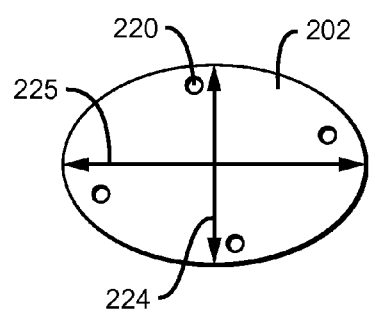
FIG. 2D is a top view of the body region of FIG. 2A.

FIGS. 2A-2C illustrate different exemplary tissue marker bodies. The exemplary body region shown in FIG. 2A has a first (upper) surface 202 and a second (lower) surface (not visible in FIG. 2A). A side wall region 205 connects the first and second surface. The first and second surface are both oval in shape, as can be seen in FIG. 2D, which shows a top view of this embodiment of a tissue marker body region. In FIG.

2A, the perimeter of the first and second surfaces both form oval shapes. In other variations, the perimeter of these surfaces may have different shapes. Furthermore, the first and second surfaces may also have different contours. For example, the first surface may be planar (flat) and the second surface may be curved. The first 202 and second surfaces of the body region in FIG. 2A are separated from each other by the thickness of the side wall 205. The side wall may be any appropriate thickness, though in some embodiments, the side wall is thin, or absent. In some variations, the side wall material is approximately 0.025 mm to 3 mm thick, allowing an 8G biopsy needle (having an inner diameter of approximately 3.4 mm) to fit inside. For example, the embodiment of the body region of a tissue marker shown in FIG. 2B comprises only a first and second surface, and does not include an additional side wall surface.

In FIG. 2B, the first 212 and second 213 surfaces are both shown as curved surfaces, and the perimeter of these surfaces meet to form an edge 217. In FIG. 2B the perimeter of the first 212 and second 213 surfaces form an oval having a major (long) and a minor (short) axis. As mentioned, the first and second surfaces may have any appropriate shape. For example, FIG. 2C shows an example of a body region having a first 232 and second surface that are rectangular, with a major (e.g., long) axis and a minor (e.g., short) axis. The rectangular surfaces of FIG. 2C are generally parallel and are separated from each other by a side wall 215.

The first and second surfaces may have any appropriate dimensions, although they generally include a major diameter and a minor diameter, as mentioned. FIG. 2D shows a top view of the body region shown in FIG. 2A. Lines 224 and 225 indicate the major, or long, axis and the minor, or short, axis. The major axis is generally longer than the minor axis, as mentioned above. Although all of the examples shown herein have body regions with first and second surfaces that are substantially parallel, the first and second surfaces may also be non-parallel, including perpendicular surfaces. In some variations, the minor diameter is between about 2 mm to about 3 mm. In some variations, the major diameter is between about 2 mm to about 15 mm Elongate members are generally coupled to the body of the tissue marker though one or more coupling sites. A coupling site links one or more elongate members to the body of the tissue marker, and the elongate member may be movably or rigidly coupled. Any appropriate coupling site may be used. A coupling site may be present on any part of the body region, such as the first and/or second surfaces, or the sidewall. In some embodiments, a coupling site is present on the first surface. For example a coupling site may be a mount that is attached to the first surface into which an elongate member is received. In some embodiments, the coupling site is a pit or socket in a surface of the body into which the elongate member engages. In other embodiments, a coupling site comprises a hole passing through (or in communication with) two or more surfaces of the body region. In this embodiment, an elongate member may pass completely through the coupling site, and the elongate member may project from both the first and the second surfaces of the body of the tissue marker.

Figure 8:
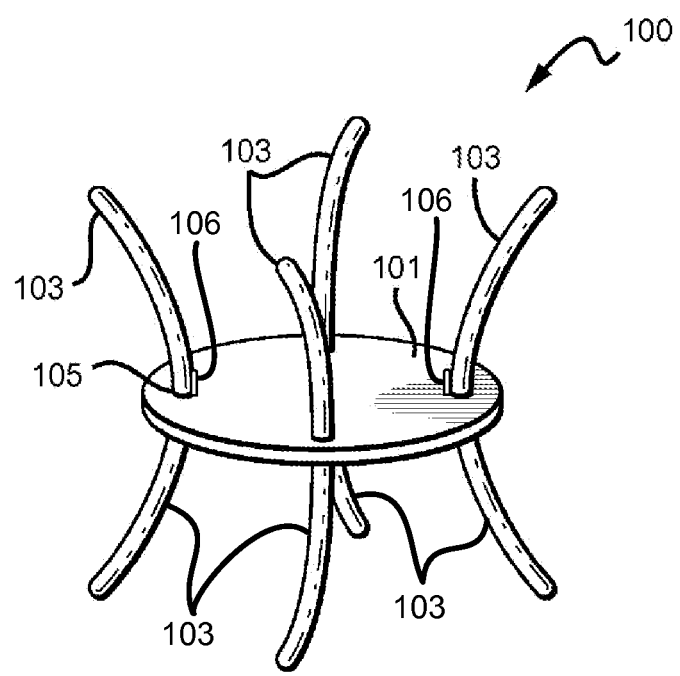
FIG. 8 is a perspective view of another embodiment of a tissue marker.

As mentioned, a coupling site may movably couple the elongate member to the body region of the tissue marker. For example, a coupling site may attach to an elongate member so that the elongate member can bend, slide and/or twist with respect to the body region of the tissue marker. In some embodiments, as illustrated in FIG. 8, the coupling site 105 includes one or more hinges 106 that permit an elongate member 103 to move. For example, one or more elongate regions may be attached to a hinge portion of a coupling site 105, and a complementary portion of the hinge 106 may be attached to the body 101, permitting the elongate member 103 to move with respect to the body 101. The coupling site may also include a pin or lock to secure the elongate member within the coupling site and prevent or inhibit movement. In some embodiments, the coupling site may include a shape-memory mount to couple one or more elongate members to a surface of the body of the tissue marker. In this embodiment the position of the elongate member with respect to the body region may be changed based on the configuration of the shape-memory alloy.

Returning now to FIGS. 1A and 1B, coupling sites 105 are shown as holes passing thought the aligned first and second surfaces of the body region 101. Thus, elongate members 103 project through the body region 101 by passing through the coupling sites 105. Although a single elongate member 103 is shown linked to a single coupling site, it should be understood that multiple elongate members may be linked to a single coupling site. Although a coupling site may permit movement of an elongate member relative to the body region, coupling sites typically prevent the elongate member from de-coupling with the body region (e.g., and separate from the tissue marker). In the embodiment shown in FIGS. 1A and 1B, the elongate member is fixed to the body region of the tissue marker. For example, an elongate member may be friction fit within the body region. An adhesive, pin, clamp, or holdfast may be used to secure an elongate member within a coupling site. In some embodiments, the coupling site comprises a threaded portion into which an elongate member screws. A coupling site may also movably couple an elongate member to a body region. For example, a coupling site may comprise a hinge, axel, pin, track, or the like, through which an elongate member may move.

The exemplary body regions shown in FIGS. 2A-2D also include coupling sites 220. In FIGS. 2A-2D, these coupling sites are shown as holes through the first and second surfaces of the body region. As mentioned above, a coupling site is not limited to a hole or passage through the body region of the tissue marker. For example, a coupling site may be a mount that attaches to the body region and projects from a surface to couple to an elongate member. Of course a mount may also be recessed within the surface (or partly within the surface). In some embodiments, the coupling site includes a region that mates with at least one region of an elongate member. For example, the coupling site may include a male region (e.g., a pin, axel, hinge, pivot, etc.) that mates with a female region (e.g., hole, groove, pit, etc.) on the elongate member, or a female region of the coupling site may mate with a male region of the elongate member.

Although the majority of examples of coupling sites provided herein describe mostly mechanical couplings, a coupling site may also non-mechanically couple an elongate member to the body of the tissue marker. For example, the coupling site may magnetically couple one or more elongate members to the body of the tissue marker. In some embodiments, the coupling site includes both mechanical and electrical and/or magnetic components.

Figure 3A:
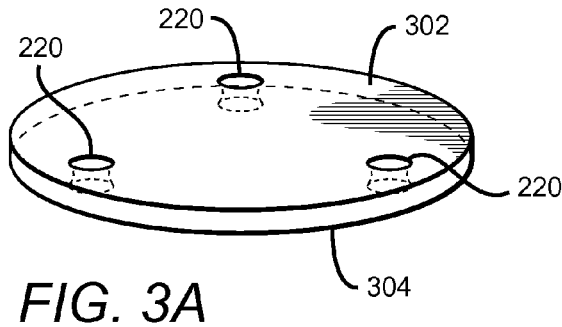
FIG. 3A is a transparent perspective view of one embodiment of a body region of a tissue marker.

FIG. 3A shows one embodiment of a coupling site 220 comprising a passageway through the body of a tissue marker. Three coupling sites are shown in FIG. 3A. Each coupling site extends from a first (e.g., upper) surface 302 of the body of the tissue marker through the body, and to a second (e.g., lower) surface 304 that is aligned with the first surface. The coupling site has an inner wall with a convex profile as it passes from the first to the second surface. An elongate member may be secured within the coupling site by having a narrow diameter region (surrounded by wider diameter regions) on its length that fits through the constricted inner region of the coupling site. In this example, the profile of the passageway of the coupling site may allow an elongate member to pivot within the coupling site with respect to the body region of the tissue marker.

In some embodiments, the coupling site also includes one or more joint members. A joint member may help secure an elongate member to the coupling site. In some embodiments, the joint member is an elastomeric or compressible material that permits the elongate member to move with respect to the body. Examples of elastomeric materials may include (but are not limited to) silicones, latex, rubbers, thermoplastic elastomers (TPE's) such as styrene-ethylene/butylene-styrene block copolymers (SEBS)-based TPE's (such as C-Flex), polysiloxane modified SEBS and their associated families, polyvinylchloride (PVC), cross-linked polyolefins such as polyethylene, and various polyurethanes. Elastomeric materials may also be compressible materials, and may also include foams, gels, and the like.

Figure 3B:
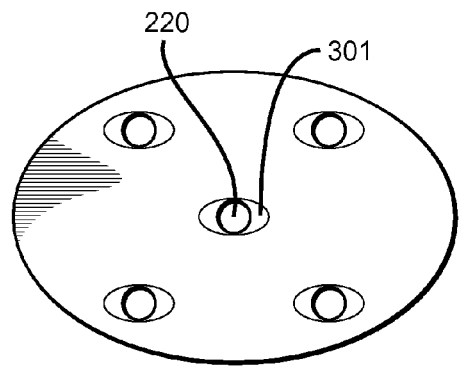
FIG. 3B is a top view of one embodiment of a body region of a tissue marker.

FIG. 3B shows a body region of a tissue marker having five coupling sites 220. Each coupling site 220 includes a joint member 301. In this example, the coupling site includes a passage between two surfaces of the body of the tissue marker. This passage has an oval cross-section, and the joint member abuts the walls of the passage, and forms a passageway through the body into which an elongate member may pass. In this embodiment, the coupling site and is configured so that an elongate member coupled to the coupling site can move (e.g., relative to the body) preferentially in one direction. In particular, an elongate member passing though the coupling site 220 can move preferentially in the direction formed by the long axis of the elliptical cross-section of the coupling site. In operation, the elongate member couple compresses the joint member against the body, since the joint member is at least somewhat compressible.

Figure 4:
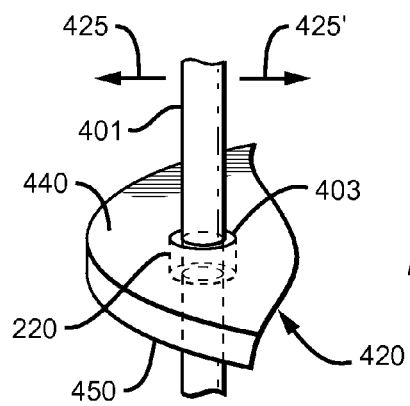
FIG. 4 is a partial view of a tissue marker near a coupling site.

FIG. 4 illustrates one embodiment of a coupling site 220, showing an elongate member 401 coupled to a portion of a body region 420 of a tissue marker. The coupling region show in FIG. 4 includes a joint member 403. In this embodiment the coupling site 220 forms a passageway through the body between the first surface 440 and the second surface 450. The coupling site is shown as a circular passageway, lined by a joint member. The joint member 403 is an elastomeric material between the body region of the tissue marker and the elongate member 401. Thus, the elongate member may bend with respect to the body region by compressing the joint member 403, as indicated by the arrows 425, 425'.

In general, a coupling site may be located in any appropriate portion of the body of a tissue marker, and any appropriate number of coupling sites could be used. For example, in FIG. 3B, five coupling sites are shown, and these coupling sites are located along the periphery of the body as well as through a central region. In FIG. 3B, the coupling sites extend through the aligned (e.g., approximately parallel) first and second surfaces of the body of the tissue marker. As mentioned above, the coupling site may couple and elongate member to only one surface (e.g., the first or second surface) of the body region. Thus, coupling sites may not be symmetrically arranged across the body of the tissue marker.

One or more elongate members typically extend from the body region of the tissue marker and are coupled to the body region through coupling sites. An elongate member may have any appropriate length, curvature and cross-section. For example, the elongate member may have a circular cross-section, a tear-drop cross section, and oval cross-section, a polyhedral cross-section, or some combination thereof. In some embodiments the elongate member is bifurcated (e.g., branches). An elongate member may be straight or curved, and may have a uniform cross-section along its length, or the cross section may vary along the length. In some embodiments, the elongate member tapers as it extends from the body of the tissue marker. The elongate member may be solid, porous, tubular, or some combination thereof. As described above, an elongate member may be made of any appropriate material, preferably biocompatible materials including metals, polymers, ceramics, or some combination of materials. In addition, an elongate member may also include one or more bioactive materials (e.g., drugs, enzymes, etc), including bioactive materials to aid in wound healing, tissue ingrowth, or the like. Finally, as described in more detail below, the elongate members may include a material to help aid in visualizing the tissue marker.

Although many of the examples shown herein describe tissue markers having a plurality of elongate members, a tissue marker may have any number of elongate members, including a single elongate member. In some variations, the tissue marker includes more than one elongate member (e.g., 2, 3, 4, 5, 6, 7, etc.). As described herein, a single elongate member may extend through the body region and project from both sides, or the body region may include two or more elongate members that extend from the body region (and appear to pass through the body region).

Returning now to the tissue marker 100 shown in FIGS. 1A and 1B, four elongate members 103 are shown extending from the body region 101. In this embodiment the elongate member extends symmetrically from the body region by passing through the body so that they project from both the first and second surfaces. The elongate members 103 are shown as curved, extending generally away from the body region 101 in this (e.g., deployed) configuration. Thus, each elongate member is shown as a curved cylindrical member having a tapered distal end. In other embodiments, the elongate members do not pass through the body of the tissue marker, but may project only from one side, or do not symmetrically project from the body region.

An elongate member may also include one or more tissue engagement regions or attachment members. Examples of different attachment members include hooks, loops, suckers, barbs, pores, and the like. Attachment members may be located along any portion of the elongate member and may help secure the tissue marker in the tissue. In some embodiments, attachment members are located at a distal portion of the elongate member (e.g., distal from the body region). More than one attachment member may be present on an elongate member. For example, in one embodiment an elongate member includes attachment members configured as barbs along the length of the elongate member, extending from the body region of the tissue marker to the distal tip. In one variation, the attachment member is a hook. For example, the elongate member may have a hook at its distal end.

Figure 5:
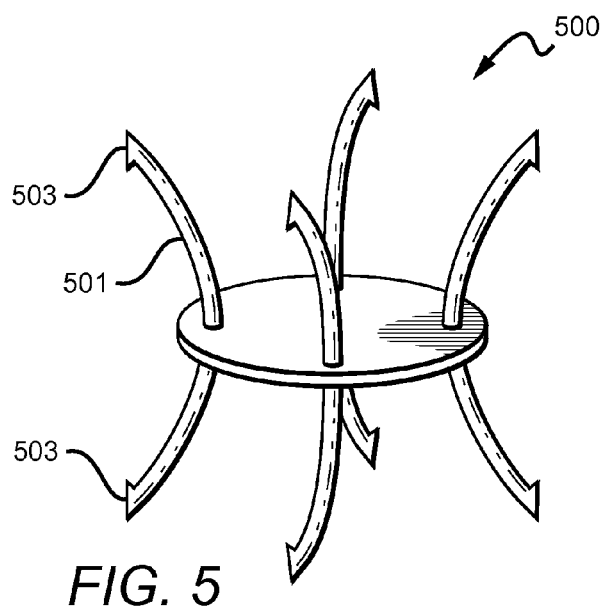
FIG. 5 is a perspective view of another embodiment of a tissue marker.

FIG. 5 shows another embodiment of a tissue marker 500 having elongate members 501 with attachment members 503 (shown here as barbs) at the distal ends of each elongate member. The elongate members 501 in FIG. 5 are also curved; however it should be understood that (in general) elongate members may be straight, or bent instead of (or in addition to) being curved. Furthermore, the direction of any curve or bend may be different from that shown in FIGS. 1A, 1B and 5. For example, in some embodiments, the elongate members curve or bend inwards. In some embodiments, the elongate members may extend in a generally first direction and then in a different generally second direction.

A tissue marker may include more than one elongate member, and any of the elongate members included as part of the tissue marker may have different properties. For example, different elongate members of a tissue marker may have different lengths or curvatures. Furthermore, as mentioned above, the position and relationship of the elongate members with respect to the body region of the tissue marker may be configured to change. For example, the elongate members may be configured to bend with respect to the body region.

As previously described, a coupling site may allow an elongate member to move with respect to the body region. Furthermore, an elongate member may itself bend or flex. In some embodiments, the elongate member is made of a material that permits such movement. For example, the elongate member may be made of a material that permits it to change shape from an initial configuration (and preferably later to return to the initial configuration). Thus, the elongate member may be made (at least in part) of a shape-memory alloy, or an elastomeric material, or the like. In some embodiments the elongate member comprises a hinged joint region.

The tissue markers described herein may therefore have more then one configuration, including a deployed configuration and a delivery configuration. In general a deployed configuration is the configuration that a tissue marker assumes when it is relaxed (e.g., when there are no substantial net forces acting upon the tissue marker or regions of the tissue marker) and/or when the tissue marker is released into a tissue. A delivery configuration is the configuration that the device assumes when the tissue marker is compressed into a smaller-profile shape (e.g., for insertion into tissue). Typically, the deployed configuration of a tissue marker allows engagement of the tissue marker with any surrounding tissue. Thus, in a deployed configuration the elongated members of a tissue marker are expanded, extending from the central region of the tissue marker (in some embodiments, the body region of the marker) to stably contact tissue.

A tissue marker may have multiple delivery and/or deployed configurations, since there may be numerous ways to configure (and/or compress) any particular tissue marker. In some embodiments, the tissue marker is configured to be inserted into tissue through a tubular (e.g., needle) inserter, and therefore the delivery configuration is compatible with a tubular inserter. As described briefly above, any region of the tissue marker, including the elongate members and body region, may be configured to change shape from a deployed configuration into delivery configuration (and vice versa). For example, the body of the tissue marker may be configured to bend or curl and more readily fit within a cannula, catheter, sheath or other device utilized for delivery. In some embodiments, the tissue marker may be compressed from a deployed configuration into a delivery configuration. A tissue marker may also have more than one delivery configuration, or more than one deployed configuration. In some embodiments, the tissue marker changes between a delivery and a deployed configuration by moving the elongate members with respect to the body. The in some embodiments, the body region does not substantially change shape. For example, the elongate members may bend (or the coupling sites to which they are attached may move), while the body remains relatively fixed.

Figure 6A:
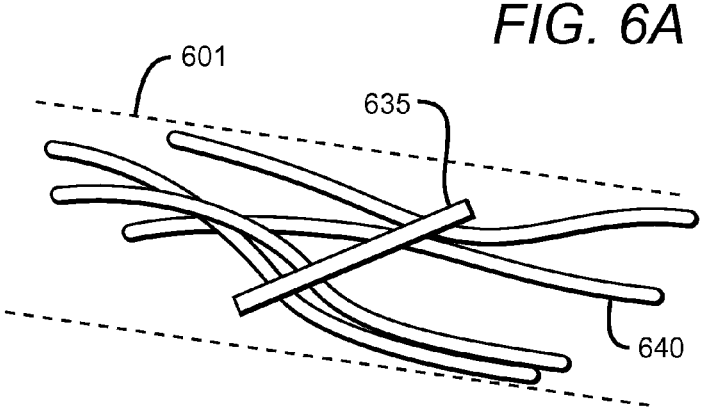
FIGS. 6A and 6B are side views of a tissue marker in a delivery configuration and a deployed configuration, respectively.
Figure 6B:
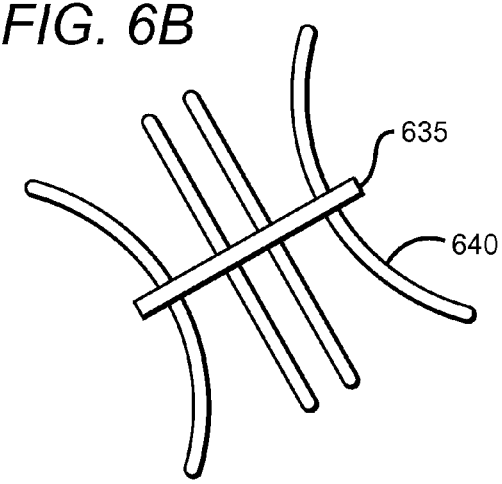

FIGS. 6A and 6B illustrate a tissue marker in a delivery and a deployed configuration, respectively. In FIG. 6A the tissue marker is shown in a delivery configuration within a cannula 601. In this example, the elongate members 640 extend approximately parallel to the walls of the cannula 601, and the body region 635 is angled so that it more easily fits within the cannula. The body region 635 in this example is generally longer than it is wide (e.g., it forms an oval or rectangular shape having a first and second surface each with a major diameter that is larger than a minor diameter), so that tilting the body region may pass through the opening of the cannula. The cannula may be part of a storage or delivery device (as described in detail below). In FIG. 6B, the tissue marker is shown in a deployed configuration, in which the legs 640 extend fully from each other and from the body region 635.

A tissue marker may be implanted into a tissue so that it can be visualized within and mark a location within the tissue. Thus, any of the tissue markers described herein may include one or more remotely visible materials allowing them to be visualized once they have been inserted into the tissue. In some embodiments, the shape or texture of all or a portion of the tissue marker may aid in remotely visualizing the marker. Furthermore, in some embodiments, the tissue marker may include an active signaling component for transmitting a signal from the tissue marker to a remote receiving device. Examples of methods of remotely visualizing a tissue marker may include (but are not limited to) x-ray based scanning techniques (e.g., fluoroscopy, angiography, CT Scanning, etc.), radiation-based scanning (e.g., PET/SPCT, NMR), magnetic-based scanning (MRI), sound-based scanning techniques (e.g., ultrasound), and the like.

For example, in some embodiments all or a portion of the tissue marker may include a radiopaque material that is remotely visible (e.g., particularly during x-ray or radiation-based scans). Radiopaque materials are well-known, and include many biocompatible metals, compounds and polymers. For example, metals such as gold, titanium, and compounds containing barium sulfate, bismuth, and tungsten have all been used as radiopaque materials. In some embodiments, all or a portion of the tissue marker may include a ferromagnetic or paramagnetic material (e.g., an iron oxide), that is visible using magnetic-based scanning (e.g., MRI). In some embodiments, the tissue marker comprises a non-ferromagnetic metal or material that is MRI compatible. Materials having a high ultrasound reflectivity may generally be visualized using ultrasound. Materials having a high contrast of acoustic impedance reflect and scatter ultrasonic energy. An example of such a material includes a material having gas-filled internal pores, or other materials having regions of discontinuous acoustic reflectivity.

Many of the tissue markers described herein may be visualized using more than one visualization modality. Thus, a single tissue marker may include more than one remotely visible material, or a remotely visible material that can be visualized under different modalities (for example, a material that is both radiopaque and ferromagnetic). Furthermore, an active signaling component may also be included as part of the tissue marker to transmit a signal from the tissue marker to be detected by a remote receiving device. For example, the tissue marker may include a miniaturized RF transmitter, a piezoelectric transmitter, or other signal transmitter. The signal may act as a beacon (e.g., indicating location) or may encode information about the surroundings or status of the tissue marker.

In general, a remotely visible material may be included in any portion of the tissue marker. For example, the remotely visible material may be included in the body (or a portion of the body) of the marker, or in one or more of the elongated members coupled to the body or in a coupling site or in a region attached to one of these sites. In some embodiments, the entire tissue marker is remotely visible under one or more of the modalities described above.

Any of the tissue markers described herein may be inserted into tissue using a delivery device or system. In general, a delivery device includes a sheath in which the tissue marker may be positioned. As described briefly above, the tissue marker can be positioned within the sheath or other region of the delivery device in a delivery configuration. The delivery device may also include a delivery actuator for controllably propelling the tissue marker from the sheath and into a tissue. Thus, a delivery system may include a delivery device (including a sheath and a delivery actuator) and one or more tissue markers. The tissue marker is preferably pre-loaded into the sheath of the delivery device. The sheath of a delivery device may be, for example, a cannula, or a region connectable to a cannula. In some embodiments, a tube or cannula is preferred, because it can be readily inserted into tissue before releasing the marker into the tissue. For example, the delivery device may be part of a biopsy needle, or may be used in conjunction with a biopsy needle. The tissue marker may then be pre-loaded into the lumen of the cannula so that it can be expelled through the lumen and into the tissue. In some embodiments, the delivery actuator is also in communication with the lumen of the cannula where the tissue marker has been loaded.

Figure 7:
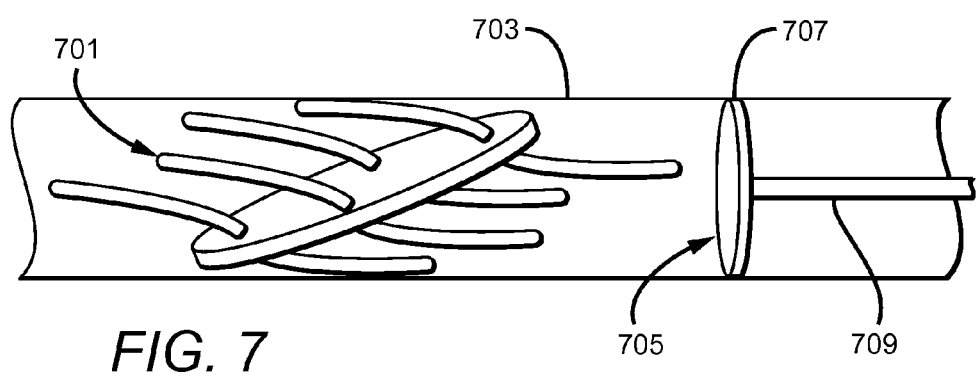
FIG. 7 is a side view of one embodiment of a tissue marker delivery system.

FIG. 7 shows one embodiment of a tissue marker delivery system. In FIG. 7 a sheath (shown as a tube or cannula) 703 is loaded with a tissue marker 701 in a delivery configuration, and a delivery actuator (shown as a pusher element 705) is positioned to push the tissue marker through the lumen of the sheath and into the tissue. The pusher element 705 in this example is configured as a piston, having a piston head 707, and a piston arm 709, and is shown immediately distal to the loaded tissue marker. In general, a pusher element may be any physical actuator configured to push a tissue marker from the sheath. When the distal end of the sheath has been positioned appropriately for delivery of the tissue marker, the piston arm portion of the pusher element may be moved to expel the tissue marker from the sheath. Thus, the pusher element may be manipulated by a medical professional acting from the proximal (e.g., external) end of the delivery device and thereby implant the tissue marker. Pushing the pusher element distally may cause the piston head to push the tissue marker from the lumen of the sheath.

A delivery actuator typically acts to apply force to expel the tissue marker from the sheath of the delivery device and into the tissue. Thus, the delivery actuator may push or pull the tissue marker from the sheath into the tissue by any appropriate means. In addition to the plunger-type delivery actuator illustrated in FIG. 7, other types of delivery actuators may be used. Other examples of actuators include other mechanical actuators (e.g., pullers, sliders, etc.), pneumatic or hydraulic (e.g. pressure) actuators, magnetic actuators, or the like. For example, a pneumatic or hydraulic actuator may act by inflating a balloon to expel a tissue marker.

The tissue markers and/or delivery systems described herein may also be sterilized (or sterilizable) and packaged for use. In some embodiments, the tissue markers are packaged for single-use, in disposable sterile packaging. An entire delivery system (including a sheath, pre-loaded tissue marker and actuator such as a pusher element) may therefore be packaged for single use. In some embodiments, the delivery sheath and pusher element may be re-used with another tissue marker. The tissue marker may also be packaged with instructions. In some embodiments the marker is coded with an identifier (e.g., a numeric, alphanumeric, bar code, etc.). The identifier may indicate the manufacturing date, location of manufacturing, patient or procedure information, or any other appropriate information.

Although the delivery devices described above are well adapted for use with the tissue markers described herein, it should be understood that they may be used with any appropriate tissue marker, and are not limited to those described herein.

In operation, the tissue markers described herein may be inserted into a tissue by inserting the tissue marker into the tissue in the delivery configuration, and expelling the tissue marker from into the tissue so that it assumes a deployed configuration. Thus, a tissue marker delivery system as described above may be used to implant a tissue marker.

For example, using a tissue marker delivery system such as that shown in FIG. 7, the sheath of the delivery system is loaded with a tissue marker. The lumen of the delivery system sheath may be continuous with the lumen of a cannula (e.g., needle). A doctor, or other medical professional, typically positions the distal tip of this cannula within the tissue in the location where it is desirable to mark the tissue. For example, during a breast tissue biopsy, it may be desirable to mark the breast tissue at the location where the biopsy occurred. After removing a biopsy (e.g., a portion of the breast tissue), the medical professional positions the distal tip of a delivery device cannula at the site of the biopsy (or adjacent to the site) and applies force to expel the tissue marker from the sheath of the delivery device. In the embodiment described in FIG. 7, the medical professional pushes the pusher element so that the tissue marker is expelled. The tissue marker slides thorough the lumen of the sheath in the compressed delivery configuration. Once it is released from the sheath, the tissue marker expands into its deployed configuration, and embeds into the tissue.

In some embodiments, the conversion between the delivery and deployed configuration occurs because the internal energy (e.g., arising from the spring constant) stored by the tissue marker in the delivery configuration. Thus, the energy stored by compressing the tissue implant is released by allowing the tissue marker to expand back into a deployed configuration, once the restraining force (e.g., from the walls of the sheath or cannula) on the device is lessened or released. In some embodiments, the change in configuration may be due to shape-memory effects resulting from a martensite transformation. This transformation may be triggered by the change in temperature (e.g., raising the temperature from the delivery device to body temperature) after inserting the tissue marker into the tissue.

Multiple tissue markers may be inserted into the same site, or a single tissue marker may be inserted. Tissue markers may be inserted into different regions (including adjacent regions). Although the insertion method described above is specific to insertion via a delivery device having a cannula, it should be understood that other delivery devices may be used. For example, a catheter-based delivery device could also be used.

In some embodiments, multiple markers may be loaded in to the delivery system. Thus, the delivery system may be configured to hold and deliver multiple tissue markers. For example, markers may be loaded sequentially into a delivery system or in parallel. When multiple tissue markers are loaded into a delivery system a single actuator may be used to delivery one or more marker at a time. In some variations, multiple actuators loaded in parallel may be delivered by separate actuators. Any appropriate number of actuators may be preloaded into a delivery system. Tissue markers may be tethered to each other. For example, tissue markers may be tethered to one or more other tissue markers by a flexible, biocompatible (and/or biodegradable) material, as described above. In one variation, tissue markers are tethered to each other using a surgical suturing material (e.g., Poliglecaprone, Polyglactin, Polyglycolic acid, Polydioxanone, catgut, silk, polyester, stainless steel, polypropylene, polyethylene, etc.).

Once the device has been released into the tissue, the delivery cannula can be removed from the tissue, and the tissue closed off to prevent infection or contamination. Because the tissue marker can be remotely visualized, the insertion procedure can be visualized (e.g., using fluoroscopy or other visualization methods). Once the tissue marker has been inserted, it can be repeatedly visualized remotely using an appropriate or compatible visualization method. Visualization of the tissue marker may be done using the standard methods for visualizing tissue by the appropriate visualization method.

This invention has been described and specific examples of the invention have been portrayed. While the invention has been described in terms of particular embodiments and illustrative figures, those of ordinary skill in the art will recognize that the invention is not limited to the embodiments or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A tissue marker, comprising:
   a body including a plate having a first surface and a second surface, the first and second surfaces each having a plurality of coupling sites; and
   a plurality of elongate members, each elongate member extending from a coupling site on at least one of the first and second surfaces, one or more of the elongate members configured to be positioned with respect to the body in a delivery configuration and a deployed configuration different from the delivery configuration,
   wherein the first surface is generally parallel to the second surface and the first and second surfaces are separated by a side wall.

2. The tissue marker according to claim 1, wherein the side wall has a height in the range of approximately 0.025 millimeters to approximately 3 millimeters.

3. A tissue marker, comprising:
   a body including a plate having a first surface and a second surface, the first and second surfaces each having a plurality of coupling sites; and
   a plurality of elongate members, each elongate member extending from a coupling site on at least one of the first and second surfaces, one or more of the elongate members configured to be positioned with respect to the body in a delivery configuration and a deployed configuration different from the delivery configuration,
   wherein the coupling sites comprise openings in the first surface aligned with openings in the second surface, wherein the elongate members are disposed in the openings to extend in a cantilevered manner from the first surface and the second surface.

4. The tissue marker according to claim 3, wherein each of the elongate members have a first free end extending from the first surface and a second free end extending from the second surface, at least one of the first and second free ends of one or more elongate members including an attachment member configured to engage bodily tissue.

5. The tissue marker according to claim 4, wherein the attachment member comprises a hook, and the hook is oriented toward a central longitudinal axis of the marker in the delivery configuration.

6. A tissue marker, comprising:
   a body including a plate having a first surface and a second surface, the first and second surfaces each having a plurality of coupling sites; and
   a plurality of elongate members, each elongate member extending from a coupling site on at least one of the first and second surfaces, one or more of the elongate members configured to be positioned with respect to the body in a delivery configuration and a deployed configuration different from the delivery configuration,
   wherein the elongate members are configured such that the elongate members are positioned generally perpendicular to the body in the deployed configuration and generally oblique to the body in the delivery configuration.

7. A tissue marker, comprising:
   a body including a plate having a first surface and a second surface, the first and second surfaces each having a plurality of coupling sites; and
   a plurality of elongate members, each elongate member extending from a coupling site on at least one of the first and second surfaces, one or more of the elongate members configured to be positioned with respect to the body in a delivery configuration and a deployed configuration different from the delivery configuration,
   wherein one or more of the coupling sites includes a hinge coupled to each of an elongate member and one of the first surface and the second surface.

8. A tissue marker, comprising:
   a body including a plate having a first surface and a second surface, the first and second surfaces each having a plurality of coupling sites; and
   a plurality of elongate members, each elongate member extending from a coupling site on at least one of the first and second surfaces, one or more of the elongate members configured to be positioned with respect to the body in a delivery configuration and a deployed configuration different from the delivery configuration, wherein both of the first and second surfaces are curved, and configured such that a circumferential edge of the first surface is connected to a circumferential edge of the second surface.

9. A delivery system, comprising:
   a sheath including a lumen;
   a pusher element disposed in the lumen; and
   a tissue marker disposed in the lumen distal of the pusher element, the tissue marker comprising:
      a body including a plate having a first surface and a second surface, the first surface being separated from the second surface and having a plurality of coupling sites; and
      a plurality of elongate members, each elongate member extending from a coupling site on at least one of the first and second surfaces, one or more of the elongate members configured to be positioned with respect to the body in a delivery configuration and a deployed configuration different from the delivery configuration, at least one of the body and one or more of the elongate members including a remotely visible material,
      wherein the elongate members are configured such that the elongate members are positioned generally perpendicular to the body in the deployed configuration and generally oblique to the body in the delivery configuration.

10. A tissue marker, comprising:

a body having a first surface and a second surface; and a plurality of elongate members, each elongate member configured to have a free end, and each elongate member being coupled to the body to extend in a cantilevered manner from one of the first surface and the second surface, wherein the body is a plate having the first surface separated from the second surface in a direction of the extent of the elongate members from the body.

11. A tissue marker, comprising:

a body having a first surface and a second surface; and a plurality of elongate members, each elongate member configured to have a free end, and each elongate member being coupled to the body to extend in a cantilevered manner from one of the first surface and the second surface, wherein at least one of the elongate members is configured to pass though an opening in the body and has two opposing free ends, and is configured such that a first free end of the two opposing free ends extends in a cantilevered manner from the first surface and a second free end of the two opposing free ends extends in a cantilevered manner from the second surface.

* * * * *